(12) United States Patent
Heideman et al.

(10) Patent No.: US 6,956,982 B1
(45) Date of Patent: Oct. 18, 2005

(54) INTEGRATED OPTICAL LIGHTGUIDE DEVICE

(75) Inventors: René Gerrit Heideman, Oldenzaal (NL); Paul Vincent Lambeck, Enschede (NL); Gerrit Jan Veldhuis, Deurningen (NL)

(73) Assignee: Universiteit Twente, Enschede (NL)

( * ) Notice: Subject to any disclaimer, the term of this patent is extended or adjusted under 35 U.S.C. 154(b) by 0 days.

(21) Appl. No.: 09/693,803

(22) Filed: Oct. 20, 2000

Related U.S. Application Data

(63) Continuation of application No. PCT/NL99/00222, filed on Apr. 16, 1999.

(30) Foreign Application Priority Data

Apr. 20, 1998 (NL) ................................. 1008934

(51) Int. Cl.[7] ............................................. G02B 6/12
(52) U.S. Cl. .............................. 385/14; 385/5; 385/12
(58) Field of Search ............................... 385/5, 12–14, 385/37; 422/82.05, 82.09, 82.11; 436/164, 436/172

(56) References Cited

U.S. PATENT DOCUMENTS

| | | | |
|---|---|---|---|
| 4,753,505 A | | 6/1988 | Mikami et al. |
| 4,790,614 A | * | 12/1988 | Imoto et al. .............. 350/96.12 |
| 4,917,450 A | | 4/1990 | Pocholle et al. |
| 5,137,359 A | | 8/1992 | Steele |
| 5,210,404 A | * | 5/1993 | Cush et al. .................. 250/216 |
| 5,253,037 A | * | 10/1993 | Klainer et al. ............... 356/133 |
| 5,280,172 A | * | 1/1994 | Di Bin et al. ........... 250/227.21 |
| 5,737,457 A | | 4/1998 | Saini et al. |
| 5,854,870 A | * | 12/1998 | Helmfrid et al. ............ 385/122 |
| 5,864,641 A | * | 1/1999 | Murphy et al. ................ 385/12 |
| 5,930,437 A | * | 7/1999 | Nakai et al. ................. 385/129 |
| 6,058,226 A | * | 5/2000 | Starodubov ................... 385/12 |
| 6,395,558 B1 | * | 5/2002 | Duveneck et al. ........... 436/172 |
| 6,603,902 B1 | * | 8/2003 | So ............................... 385/37 |

FOREIGN PATENT DOCUMENTS

| | | |
|---|---|---|
| EP | 0495413 | 7/1992 |
| EP | 0534670 | 3/1993 |

OTHER PUBLICATIONS

Article "An integrated optical Bragg-reflector used as a chemo-optical sensor", by Veldhuist, et al, dated Jan. 1, 1998, IOP Publishing LTD.
Article "Single-mode/multimode waveguide electro-optic grating coupler modulator", by Wang, et al., Applied Physics Letters, 66, nr. 20, May 15, 1995.

* cited by examiner

*Primary Examiner*—Juliana Kang
(74) *Attorney, Agent, or Firm*—Jones Day

(57) ABSTRACT

In an integrated optical lightguide device including a light-transmitting core layer, an inclusion or buffer layer, and an active or cladding layer. The cladding layer is divided into segments. Groups of different segments exhibit different refractive indices, light intensity profiles or different degrees of sensitivity which have been effected by different methods. Thus, repeated adjustable or controllable transmission has resulted in an extremely sensitive waveguide system for a sensor, a modulator, or a spectrophotometer.

24 Claims, 10 Drawing Sheets

INTEGRATED OPTICAL LIGHTGUIDE DEVICE

CROSS REFERENCE TO RELATED APPLICATIONS

This application claims priority and is a continuation of International Application No. PCT/NL99/00222, filed Apr. 16, 1999, which claims priority of Netherlands Patent Application No. 1008934, filed Apr. 20, 1998.

STATEMENT REGARDING FEDERALLY SPONSORED RESEARCH

Not applicable.

BACKGROUND OF THE INVENTION

1. Field of the Invention

The invention relates to integrated optical lightguide devices and more particularly to optical waveguide sensors, modulators and spectrophotometers.

2. Description of the Related Art

Integrated optical sensors are known from an article entitled "Fabrication and Packaging of Integrated Chemico-Optical Sensors" by R. G. Heideman et al., published in *Sensors and Actuators*, volume B 35–36, 1996, pp. 234–240. Besides sensors and actuators in a general sense, the article describes in particular a Mach-Zehnder interferometer including a deposited film, which is sensitive to air humidity. The article furthermore describes an embodiment wherein an optical fiber for light supply is integrated in the Mach-Zehnder sensor.

Generally, such a device is much too complicated for practical applications and also relatively costly, and in some cases it is sensitive to interfering parameters or to small deviations between intended and realised local refractive index profiles.

The operation of known integrated optical sensors and actuators, such as the Mach-Zehnder interferometer, is usually based on a phase change of the light being used, induced by a controlling parameter (actuator) or a parameter to be measured (sensor). This imposes restrictions as to the type of light sources to be used. For the lightguide structures to be used this means that transitions to and from elements in the optical structure will have to be provided very gradually in the direction of light propagation, resulting in relatively long structures.

U.S. Pat. No. 4,913,519 (corresponding to WO 8908273) also discloses an optical sensor structure wherein an optical fiber is covered with a periodic, interrupted cladding layer in such a manner that a parameter to be detected, a change from water to ice and from ice to water, causes the sensor operation to switch between an "off" condition where there is no light transmission when water is present and an "on" condition where light is transmitted when the water changes to ice. This patent illustrates the use of segments of identical length which are periodically spaced, but is otherwise very limited in application.

BRIEF SUMMARY OF THE INVENTION

The object of the invention is to obviate the above drawbacks. The object is accomplished by an integrated optical lightguide device of the kind mentioned in the introduction in which a material is incorporated where the value of the refractive index depends on an external physical or chemical parameter. The device is divided in a light propagation direction into a series of several types of segments each having different specific refractive index distributions. The segments may take a variety of different shapes, sizes and spacings and may be in the form of sensor material filled recesses or altered cladding regions. The segmentation may relate to a slab-type lightguide as well as to a channel-type lightguide. This optical lightguide device can, for example, be used as a sensor, as an intensity modulator and as a spectrophotometer.

The invention is essentially based on the knowledge that when a guided light beam passes through a boundary surface between two light-transmitting segments having different refractive index profiles, the portion of the light that is transmitted by the boundary surface as a guided beam within the light-transmitting structure and the light that is radiated is determined by the difference in the refractive indices of the two light-transmitting parts and of differences in guided mode field profiles. When a change in the value of an external physical or chemical parameter directly or indirectly causes the refractive indices on either side of the boundary surface to change, the consequent changes in the effective refractive indices and the mode field profiles will produce a change in the amounts of light reflected on the boundary surface, in the light beams transmitted by the boundary surface as guided modes, as well as in the light emitted on the boundary surface in the form of radiating modes. Thus, the change in the amount of light transmitted as a guided light beam is determined by and constitutes a measure of the change in the external parameter. Instead of the light transmission, the amount or the distribution of the light converted into radiating modes and/or the amount of reflected light may function as a measure of the change in the external parameter. Essential in this respect is the fact that the intended effect does not depend on the degree of coherence of the light being used, and consequently it is possible to use inexpensive, non-coherent light sources, such as light emitting diodes (LEDs), fluorescent lamps, halogen lamps, Xenon lamps, etc., as a light source instead of relatively expensive gas lasers, solid matter lasers and/or laser diodes.

Although the changes may be relatively small in the case of a single transition, the use of many transitions succeeding each another in the direction of light propagation may produce significant effects. Essential in this respect is that repetition of the transitions, and thus of the segments of parameter sensitive material or sensor material, does not need to be periodical because the operating principle is not based on phase information of the light being used, although a device according to the invention may use periodically repeated segments.

The lightguide described here is formed of layers, including a carrier, a first inclusion layer, a light transmitting layer and a second inclusion layer. If suitable specifications are used, in particular with regard to the refractive index, the carrier can also function as a first inclusion layer.

The forming of such layer structures can be done with well-defined, controllable techniques which are well known to those skilled in the art. Thus, layers having a precisely defined thickness and composition can be formed by means of evaporation, sputtering, indiffusion, CVD techniques and the like. In one preferred embodiment, channel-type lightguides are formed in the layer structures by means of photolithographic and etching techniques, for example. In a device according to the invention, the parameter sensitive material is formed of segments of at least two different types. Segments belong to the same type if they have the same refractive index profiles and mode field profiles in a plane perpendicularly to the propagation direction of the lightguide. Accordingly, segments of the same type are influenced to the same degree by the parameter to which the segments are sensitive. The dimensions of such segments, measured in the propagation direction of the lightguide, range between approximately one micron and a few dozen microns.

Sensitive segments contain a material whose refractive index depends on the quantity of an external parameter, also known as a measurand. These materials include for example chemo-optical transduction materials whose refractive indices depend on the concentration of a specific substance or of several substances. Besides the above materials, thermo-optical, electro-optical, magneto-optical, opto-optical and elasto-optical materials can be used, which material can be activated by, respectively, a temperature change, an electric field, a magnetic field, a change in light intensity and a mechanical stress.

In another preferred embodiment, two types of aligned segments, where each type exhibits a different degree of sensitivity to a specific parameter.

In yet another preferred embodiment, one of the aligned two segments has zero sensitivity to the parameter. In this case, the sensitive segments are monotype segments which are separated by segments insensitive to the measurand, and these are called bridge segments.

Parameter sensitive segments may be formed by:
the local removal of portions of a light sealing layer covering the light-transmitting layer, and optionally also removing at the same time portions of the underlying light-transmitting layer, or
the local removal of the light-transmitting layer, or
the local application of a new layer.

If there is removal, spaces thus formed are filled partially or entirely with a material exhibiting a different degree of sensitivity than the removed material, or if there is locally applied new material, it exhibits a different degree of sensitivity than the material covered.

The spaces may be filled entirely or partially with a liquid or a gas as the sensitive material whose composition determines the refractive index of the segments containing the liquid or the gas. This structure is especially suitable for measuring the composition of a liquid or a gas mixture or for determining the concentration of substances dissolved in the liquid.

The local removal of inclusion material can be done mechanically, such as by stamping or by photolithography and etching. Thus, a large number, for example hundreds, of aligned segments can be formed on a relatively short waveguide, such as a waveguide having a length dimension of one mm to a few mm. The above also applies if there are more than two different types of segments.

As mentioned, such segments may have unequal dimensions and/or be spaced unequal distances apart. The positioning and dimensions of different types of segments can be selected at random, so that an extra degree of freedom is obtained.

Another preferred embodiment of the invention is formed of two types of segments, one of which is parameter sensitive, while the other is not. In this embodiment the refractive indices of the bridge material and the sensor material are related to each other with a view to achieving optimum sensitivity for variations of the parameter within a particular range. The relationship implies that a value of the parameter exists within the particular range with a corresponding value of the refractive index of the sensor material being equal to that of the bridge material or the light-transmitting material. This is called the working point of the sensor material.

The bridge material for a lightguide used to measure relative humidity may include SiON having a refractive index of 1.50, and a material sensitive to air humidity may begelatin having a refractive index range of 1.53–1.47 in the air humidity range of 0–100%. By increasing the number of segments it is possible, using the same materials, to obtain excellent sensitivity to air humidity over a smaller part of the refractive index range to be measured around the air humidity value which corresponds with a gelatin refractive index of 1.50. This is sometimes called a peak response and it may be used as a switching pulse in an electronic circuit designed for that purpose. The selection of a refractive index of 1.53 for the bridge material makes it possible to measure refractive index values in the range of 1.52–1.53 with great precision. This range corresponds with an air humidity between of 90–100%. A chemical sensor giving peak responses may be useful for measuring the composition of a liquid or a gas mixture for the purpose of checking chemical processes, or for use in alarm systems to signal the exceeding of humidity limits, or to signal the occurrence of undesirable air or water pollution.

In another preferred embodiment, a ridge-type light-transmitting channel having a constant cross-sectional dimension, includes in the inclusion layer alternately parameter sensitive segments and generally non-sensitive segments over the entire width of the mode field profile.

In still another preferred embodiment, a ridge-type light-transmitting channel has two types of segments of identical material but differing from each other in channel widths. Even though the segments are of different widths, they are related in that the mode field profiles of each is substantially identical for a relevant value of a parameter quantity. Furthermore, when the value of the measurand changes, the mode field profiles of the two segments will also change but in an opposite sense, that is, the mode field profile of one of the two segments will become wider, and the mode field profile of the other of the two segments will become narrower. Thus, more light will be converted to radiating modes and be reflected at one segment than at the other and less light will be transmitted as guided modes while the opposite is true at the other segment.

In another preferred embodiment of a sensor, a reference channel which will not come into contact with the parameter carries out absolute measurements.

Parameter sensitive segments may be formed by local physical and/or chemical treatment of the inclusion layer material and/or of the light-transmitting material. Inclusion layer material can be deactivated partially or entirely by means of electromagnetic radiation, for example by UV irradiation, where the irradiated segments become non-sensitive or less sensitive as compared to the non-irradiated segments, or the irradiated segments react differently, at least in relation to their refractive index to such a degree that a usable signal change is obtained.

In another preferred embodiment, a strip-loaded type of light transmitting channel is formed by applying to the light transmitting layer a layer of parameter sensitive material having a constant thickness of, for example, 1–200 nm, and subsequently removing the parameter sensitive material outside the region to be defined as a channel. Alternatively, the strip may be formed by a local chemical or physical treatment either of the region to be defined as the channel or of a region that does not form any part of the channel. As a result of this local treatment, the refractive index will hardly vary, if at all, at least at a particular wavelength, and the refractive index profiles of the two types of segments will be substantially or completely identical at a zero value of the parameter, resulting in a maximum transmission of light intensity.

The parameter sensitive inclusion material may be chemo-optical material which can be used for concentration determination in biological tests, and in particular, pregnancy tests. Sensitive and less sensitive segments may be formed by local deactivation by means of electromagnetic radiation with UV light.

The light transmitting layer may be formed by homogeneously coating a parameter sensitive material having a thickness of approximately 1–200 nm. This sensitive layer is then subjected to local chemical or physical treatment, as a result of which the degree of sensitivity as well as the refractive index will change.

Since the differences in the refractive index profiles of the various types of segments will usually be small in the presence of the measurand, a relatively large number of segments will be required. These may be formed using holographic and Moire lighting techniques and pattern forming masks. These methods are especially suitable for those lightguides where a fine structure is desired (having segment length dimensions of less than 3 microns, for example), or where specific requirements apply, for example, as regards the gradients in the transitions between sensitive and non-sensitive segments.

In another preferred embodiment, sensitive segments contain an electro-optical, thermo-optical, magneto-optical, opto-optical or elasto-optical material, with the light transmission of the lightguide device to be controlled by varying, respectively, an electrical field, temperature, a magnetic field, light intensity or a mechanical stress or pressure in the material, thus forming an intensity modulator. In an alternative embodiment of the modulator, one of the layers forming the lightguide includes sensor material that is effected in segments. For example, an electric field or heat may be applied by irregularly spaced electrodes. The regions adjacent the electrodes will form the parameter sensitive segments.

ZnO is a suitable material to be effected by an electric field. Electrodes may also be used to pass a current and thereby heating material where both techniques allow variations in the refractive index profile of the material. Other materials and physical phenomena may be used for light intensity modulators through refractive index variation by external activators, such as magnetic fields, pressure, deflection and the like.

Where a light transmitting channel is formed by segments of the same material but differing widths, a non-patterned metal film may function as an electrode. When the value of the parameter changes, the mode field profiles will change in an opposite sense, that is, the mode field profile of one of the two segments will become wider, and the mode field profile of the other of the two segments will become narrower, resulting in a mode field profile mismatch as described above, and as a result the amount of light transmitted as guided modes on a boundary surface between segments will change, as will the amount of light converted into radiating modes and the amount of light reflected.

In another preferred embodiment, two types of segments are effected by different parameters. For example, one group of segments may contain a chemo-optical material, and the other group of segments may contain an electro-optical material. The cross-sectional dimensions of the two different types of segments may be the same, while the values of their refractive indices are identical for a set of relevant values for each of the different parameters. In this state, the working point of the sensor, the transmission factor of the segmented lightguide is at a maximum, $T_{max}$. When there is a refractive index change in one segment induced by a parameter A, the other segment may be forced to undergo an identical refractive index change by altering parameter B, so as to have the transmission factor equal to $T_{max}$. Thus, the value of measurand A may be correlated with the known value of parameter B. This process can be automated by means of a feedback loop.

In another preferred embodiment, the refractive index at the location of the non-sensitive segments may be optimized for wavelength measurements, such that the amount of light being transported through the lightguide is wavelength-dependent, as is the intensity distribution of the light emitted by the segments. Thus the lightguide acts as a spectrophotometer. In such a spectrophotometer, an array of photosensitive segments in the form of a photodiode array or a linear CCD chip, is used for measuring laterally emitted light. The photodiode array contains a number of photodiodes in the propagation direction of the lightguide, and the CCD chip contains a number of elements by which the exiting light can be measured as a function of the propagation direction, thus making it possible to determine a diffusion distribution. The light detector may extend along the entire lightguide length or may overlap only part of it. A light detector array may be provided on one side or on both sides of the lightguide. Both the number of photodiodes of the array and the number of parameter sensitive segments contribute to diffusion capacity.

In another preferred embodiment, parameter sensitive segments are used which do not impeded light when in a quiescent condition. When electrical excitation takes place, there is a change in the refractive index. This change is not permanent. Each excitation voltage or current is associated with a particular refractive index. The resulting refractive index profile change is different for each wavelength because the waveguide exhibits wavelength dispersion. Each wavelength that is present will pass through the system to a different degree and thus have a different transmission value. Hence, the amount of light that passes through the lightguide becomes wavelength-dependent.

In this situation, upon excitation total light transmission is measured. Then the excitation voltage or current is increased and the light transmission is measured anew. This is repeated several times in succession. Electrode voltages or currents having different values are used each time, and with each of the new values a measurement is made of the amount of light exiting from the entire system, where it is not known what wavelengths the light contains. On the basis of the amount of light determined by transmission measurements, the spectral content of the presented light can be determined, after a complete series of measurements have been made, using arithmetic algorithms. Subsequently, the excitation is turned off and all of the light will pass through the lightguide unimpeded.

A more complete understanding of the present invention and other objects, advantages and features thereof will be gained from a consideration of the following description of preferred embodiments read in conjunction with the accompanying drawing provided herein. The preferred embodiments represent examples of the invention which are described here in compliance with Title 35 U.S.C. section 112 (first paragraph), but the invention itself is defined by the attached claims.

DETAILED DESCRIPTION OF PREFERRED EMBODIMENTS OF THE INVENTION

Figure 1:
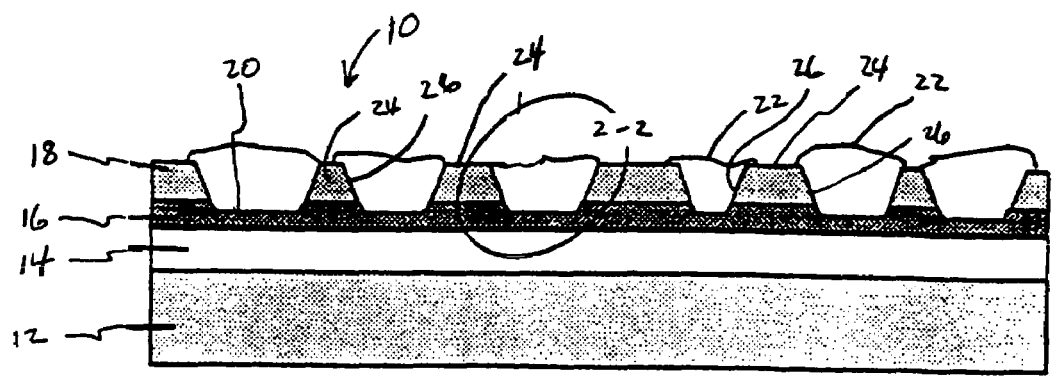
FIG. 1 is a diagrammatic longitudinal sectional elevation view of a segmented waveguide sensor or modulation.

While the present invention is open to various modifications and alternative constructions, the preferred embodiments shown in the various figures of the drawing will be described herein in detail. It is understood, however, that there is no intention to limit the invention to the particular embodiments, forms or examples disclosed. On the contrary, the intention is to cover all modifications, equivalent structures and methods, and alternative constructions falling within the spirit and scope of the invention as expressed in the appended claims, pursuant to Title 35 U.S.C. section 112 (second paragraph).

Figure 2:
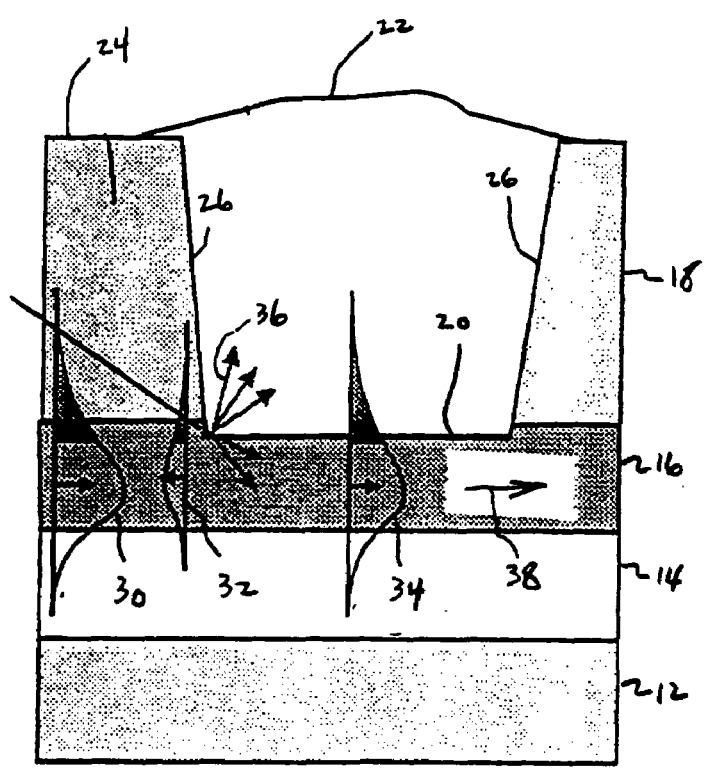
FIG. 2 is an enlargement taken within circle 2—2 of FIG. 1.

A light guide 10 according to the invention is depicted in FIGS. 1 and 2 and incldues a carrier 12, such as a silicon wafer, a first inclusion, buffer or substrate layer 14, a light-transmitting or core layer 16 and a second inclusion or cladding layer 18. Parameter sensitive segments are formed in the cladding layer 18 by creating recesses 20 which may extend into the core layer 16 also. When the lightguide is used as a sensor, for example for air humidity measurements, or measurements of the composition of gases or liquids, the recesses are filled with a medium or sensor material 22 having a refractive index which is sensitive to the parameter to be measured. Examples are gelatin and polyimide for air humidity measurements. Between the recesses 20 is cladding material 24, called a bridge segment and each boundary between two adjacent segments is called a transition 26. The parameter to be measured, also known as the measurand, for example, a gas or a liquid, fills the recesses and determines the refractive index of the segment, which refractive index is a function of the quantity of the measurand, for example, the concentration of a particular substance in the recess, or the proportion in a mixture of various liquids in the recess.

Referring now to FIG. 2, there is shown a graphic illustration of a light intensity distribution 30 in the lightguide, as well as a light reflection distribution 32 at the transition 26 and the remaining light intensity distribution 34 being transmitted in guided mode. Arrows 36 indicate that part of the incoming light beam is converted into radiating modes, which will exit the lightguide laterally. The light intensity in a propagation direction 38 may be measured as may the light being emitted laterally.

It is to be noted that the recesses 20 are not identical lengthwise nor evenly distributed. Nor is the operation of the lightguide affected if one or more of the recesses continue more deeply or less deeply into the light-transmitting or core layer or whether the core layer is covered completely. It is also to be noted that sensitivity may be increased by relating the refractive indices of the parameter sensitive segments and the bridge segments.

Figure 3:
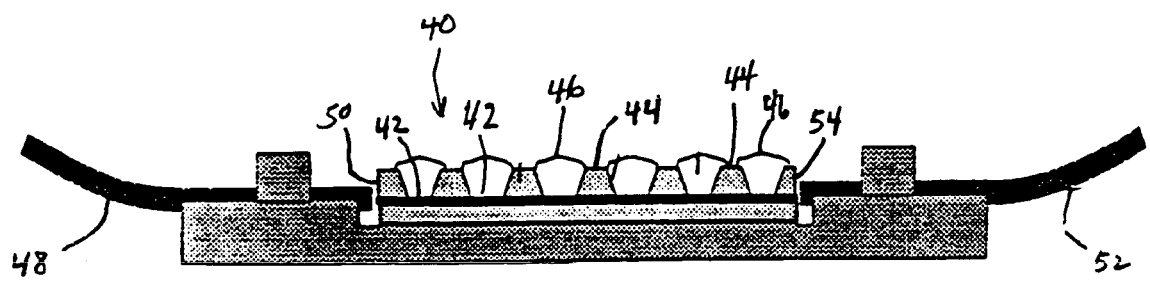
FIG. 3 is a diagrammatic longitudinal sectional elevation view of a segmented waveguide sensor or modulator with a light supply, an optical input fiber and an optical output fiber.

FIG. 3 shows an integrated optical channel-type lightguide device 40, with recesses 42 being provided in the inclusion or cladding layer 44 and where the recesses are filled with sensitive material 46. A light entry or input optical fiber 48 is provided on an entry side 50 of the lightguide and a light detection or output optical fiber 52 is provided on an exit side 54 of the lightguide. The lightguide as described may have a length of one centimeter and a width of a few millimeters, and the number of recesses it contains may range from just a few to a few hundred, depending upon the application. Also, other channel structures may similarly include a light entry optical fiber and/or a light detection optical fiber.

Figure 4:
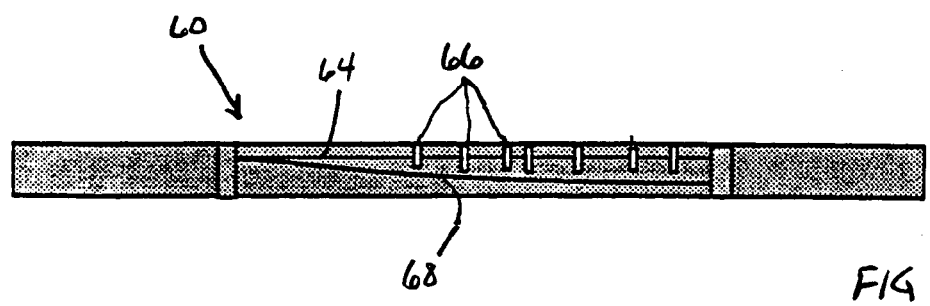
FIGS. 4 and 5 are diagrammatic top views of lightguides illustrating the use of reference channels.
Figure 5:
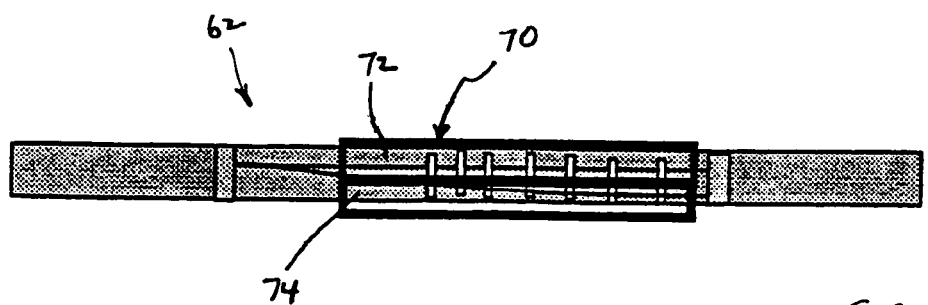

Lightguides 60, 62 as depicted in FIGS. 4 and 5 include one or more lateral channels which can be used as reference channels. This makes it possible to compensate for external influences, such as ambient temperature, partially or completely during measurement, and to realize absolute measurements. The lightguide 60 of FIG. 4 shows a measuring channel 64 with parameter sensitive segments 66 and a reference channel 68 which does not pass any parameter sensitive segments and thus is not influenced by the parameter to be measured. The lightguide 62 of FIG. 5 shows an embodiment comprising a cuvette 70, which divides the guide into a measuring cuvette 72, with parameter senstivie segments, and a reference cuvette 74, with reference segments unaffected by the measurand.

Figure 6:
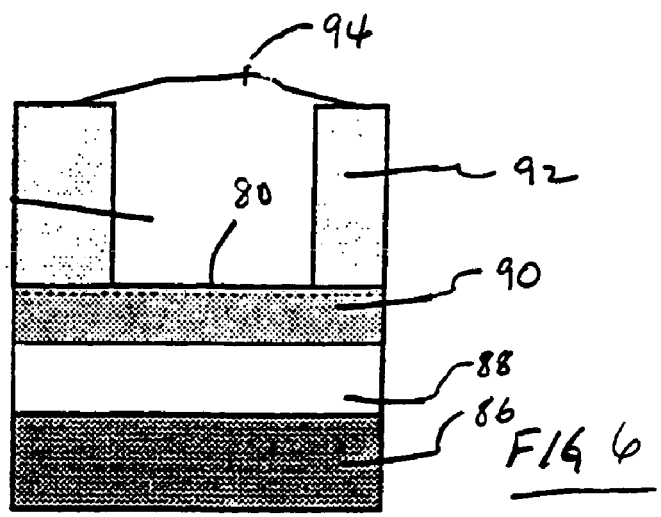
FIGS. 6, 7 and 8 are enlarged views similar to FIG. 2 but illustrating different segment geometries.
Figure 7:
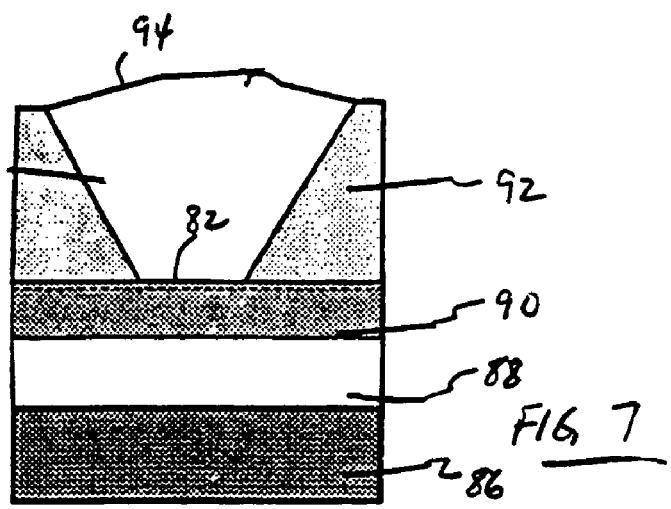
Figure 8:
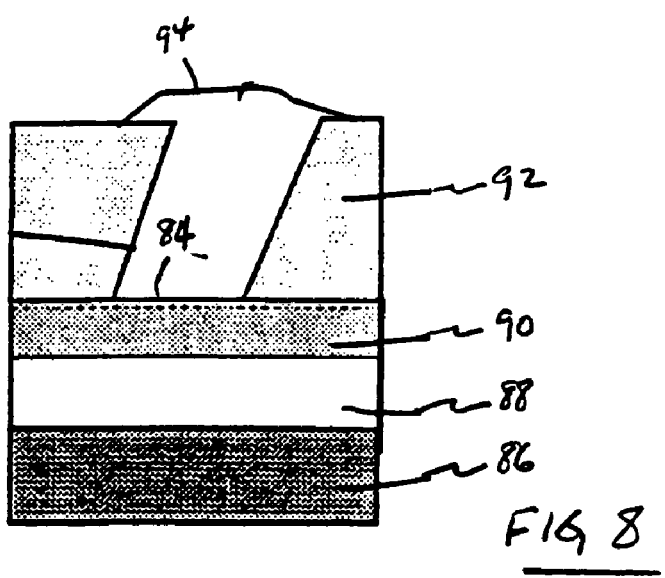

Referring now to FIGS. 6, 7 and 8, various embodiments of recess geometries for activable parameter sensitive segments are shown. These include a rectangular shaped recess 80, a conical shaped recess 82 and a parallelogram shaped recess 84. The variety of available shapes provides additional freedom in the selection of sensors or actuators. It should be noted that the degree of laterally emitted light can be varied as a function of the geometry of the recess transitions. Furthermore, the recesses may be positioned perpendicular to the propagation direction of a guided light beam or at an angle deviating from 90° thereto, or the recesses may have a different geometry than those shown.

As with the FIG. 1 lightguide, each embodiment just disclosed includes a carrier layer 86, a first inclusion layer 88, a core layer 90, a cladding layer 92 and parameter sensitive material 94 in the recesses.

It is also noted that instead of being formed by recesses, segments may also be formed by a locally deviating physical or chemical treatment of a cladding layer. Furthermore, the above mentioned different geometries may be formed in the cladding layer by the physical or chemical treatment so as to not require the removal of the cladding layer material.

Figure 9:
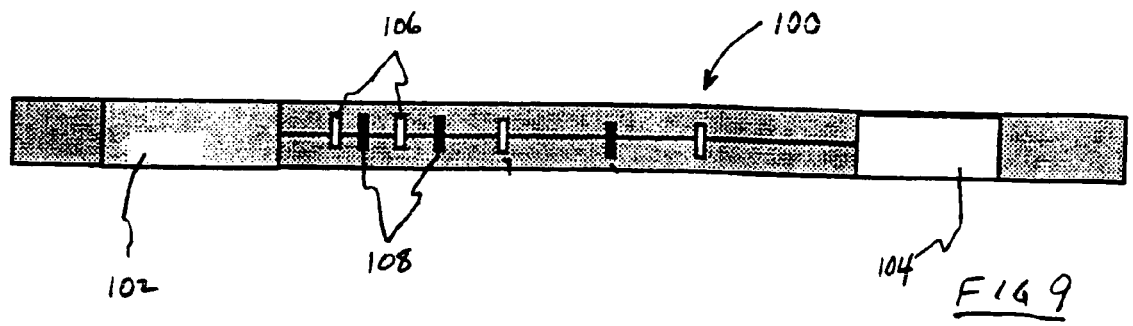
FIG. 9 is a diagrammatic longitudinal plan view of a lightguide sensor with an integrated light source and detector and illustrating the use of electrodes.

FIG. 9 shows a segmented sensor system 100 that includes an integrated light source 102, an integrated light detector 104, parameter sensitive segments 106, as well as segments 108 which are changeable with an electrode. In this case, a light source can be selected on the basis of the price, performance and its ability to integrate, since the sensor offers no phase information; hence, no monochromatic, coherent light source is required. For example, an LED or a VCSEL light source may be advantageously used. The two kinds of segments 106, 108 may be arranged to provide a feedback possibility. As explained earlier and again below, a feedback arrangement where light transmission is maintained at a maximum level may be used to determine a desired measurand.

Figure 10:
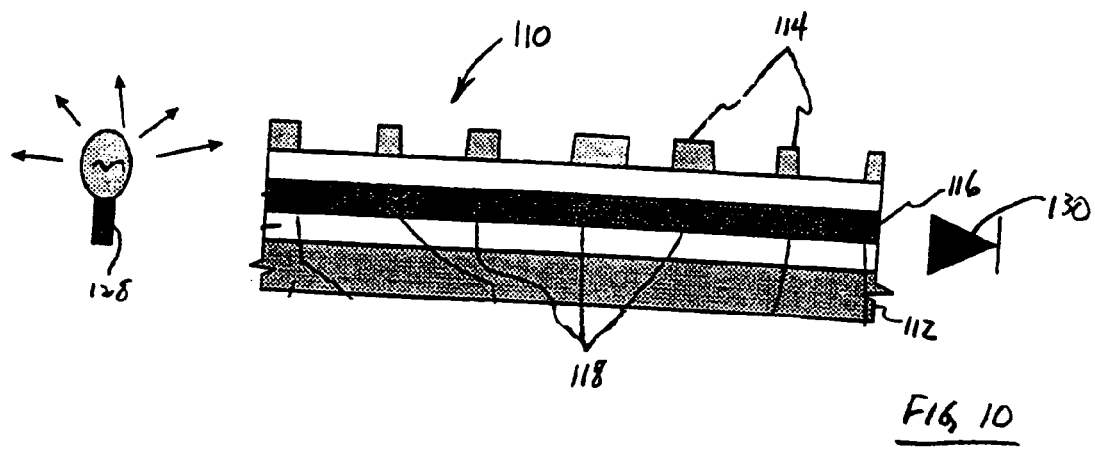
FIG. 10 is a diagrammatic longitudinal sectional view of a lightguide usable as a moduator or a spectrophotometer for determining the wavelength of monochromatic light.
Figure 11:
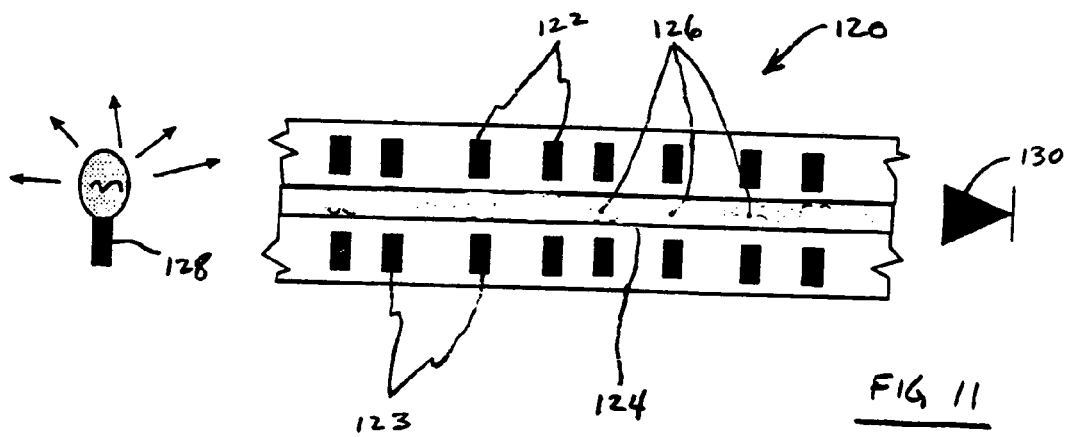
FIG. 11 is a diagrammatic longitudinal plan view of another lightguide that may be used as a modulator or a spectrophotometer.

Two embodiments of integrated optical lightguides for use as an intensity modulators are shown in FIGS. 10 and 11. The lightguide 110 shown in FIG. 10 includes a lower electrode 112, upper electrodes 114 and parameter sensitive material 116. The sensor material under the upper electrodes 114 form segments 118 whose refractive index is varied by means of electric control signals on the electrodes. As a result of the signals the refractive index at the segment locations are changed and the intensity of the transmissed light is controlled. The lightguide 120 shown in FIG. 11 may also be configured so that the parameter sensitive segments are formed by providing electrodes 122, 123 to each side of a channel 124, as a result of which the refractive index of material 126 located between the electrodes will vary upon application of a voltage. As FIGS. 10 and 11 diagrammatically indicate, the lightguides 110, 120 are each connected to a light source 128 and a light detector 130, for example, a photodiode.

The lightguides 110, 120 shown in FIGS. 10 and 11 may also be used as spectrophotometers. When there is no applied electric field, incident light will pass through the device substantially unimpeded. When an electric field is applied to the electrodes, wavelength-dependent light diffusion will occur, and a reduced amount of light will be emitted from the lightguides. By measuring the emitted light by means of the detector 130 and the value of an applied voltage, the spectral distribution of the incident light can be calculated. The spectrally dependent absorption or fluorescence of the lightguides depends on the number of segments, the sensitivity to dispersion of the transition between two neighboring segments and the number of selected values of the activating parameter.

Figure 12:
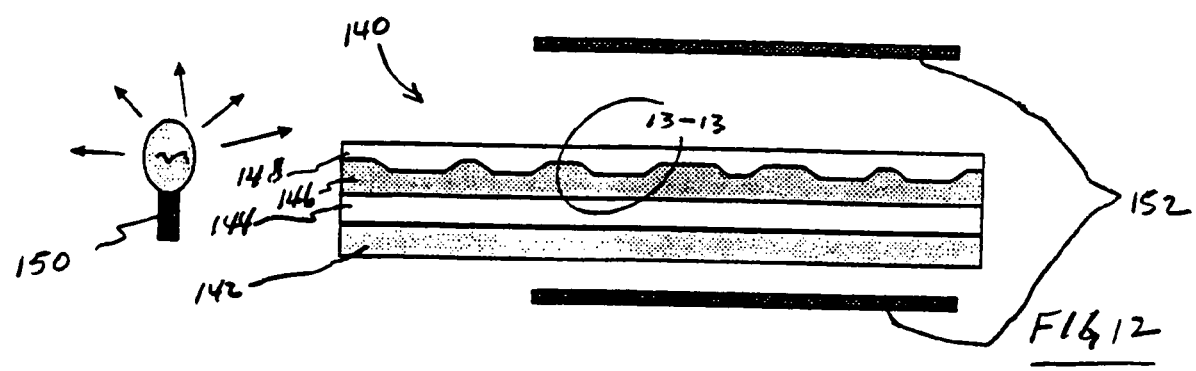
FIG. 12 is a diagrammatic longitudinal sectional elevation view of another spectrophotometer.
Figure 13:
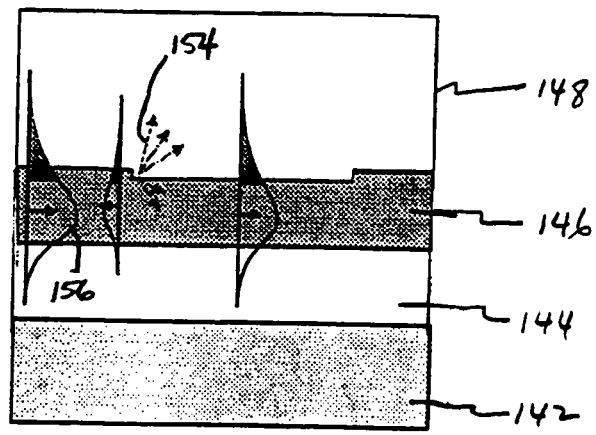
FIG. 13 is an enlargment taken within circle 13—13 of FIG. 12.

Referring now to FIGS. 12 and 13, there is illustrated a spectrophotometer 140. As in FIG. 1, there is a carrier 142, a first inclusion layer 144, a core layer 146 and a cladding layer 148. A light source 150 is provided and one or two light detector systems 152, for example, in the form of a photodiode array or a chip including a linear array of photosensitive elements.

Laterally emitted light 154, FIG. 13, from an entering guide mode 156 is measured in a locally sensitive manner by means of the light detector systems 152. In this manner a light diffusion curve and the spectral distribution of the exiting light is determined.

Figure 14:
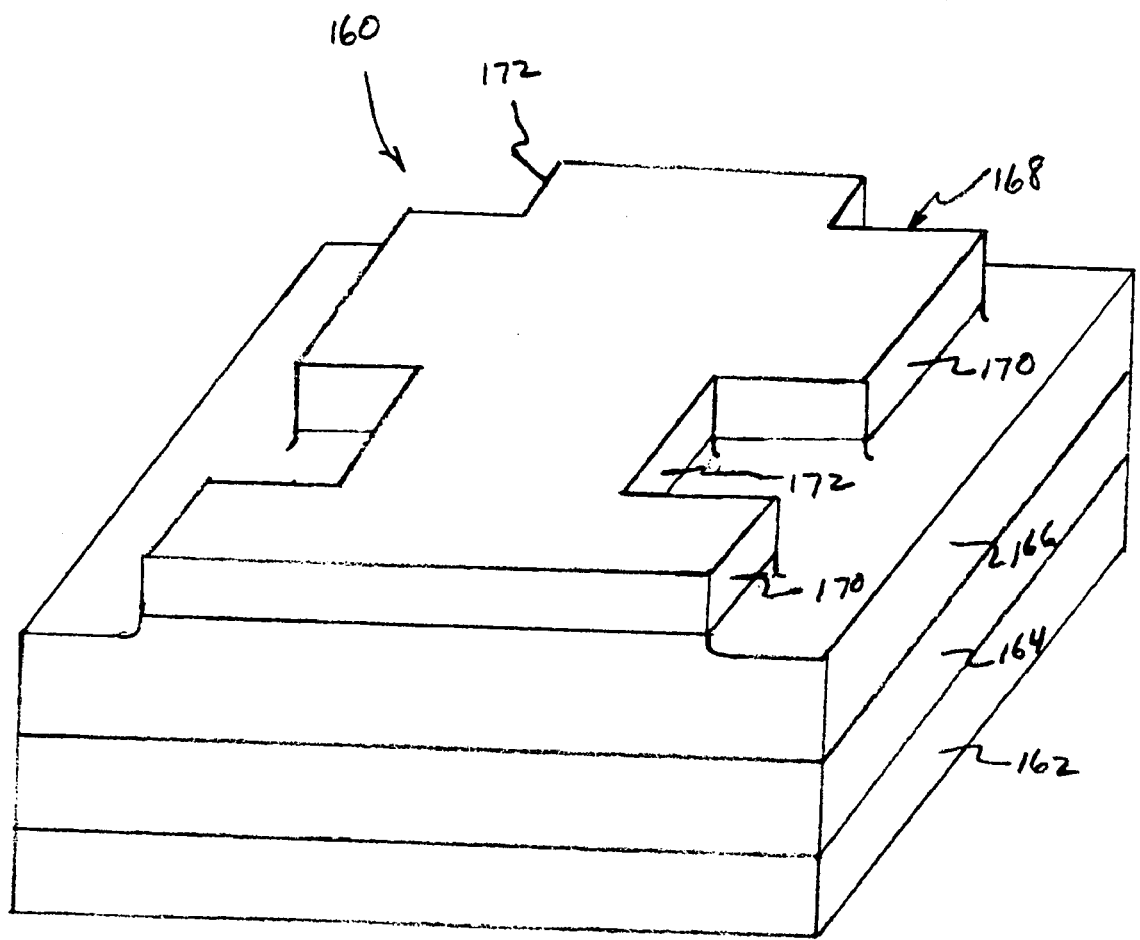
FIG. 14 is a diagrammatic isometric view of a lightguide sensor with segments of different widths.

In FIG. 14 a lightguide 160 is shown having a carrier layer 162, a substrate layer 164, a core layer 166 and a parameter sensitive cladding 168 where the parameter sensitive cladding forms two types of segments by virtue of having different widths, namely, wide segments 170 and narrow segments 172. Although the refractive indices of both types of segments 170, 172 are the same, the widths of the two types of segments are geared to each other such that when the amount of measurand is varied, the intensity distribution at each of the transitions between segments will vary inversely thereby resulting in a very sensitive lightguide. It is noted that the lengths of the segments in the direction of light propagation vary, as explained above in relation to the lightguide shown in FIG. 1.

Figure 15:
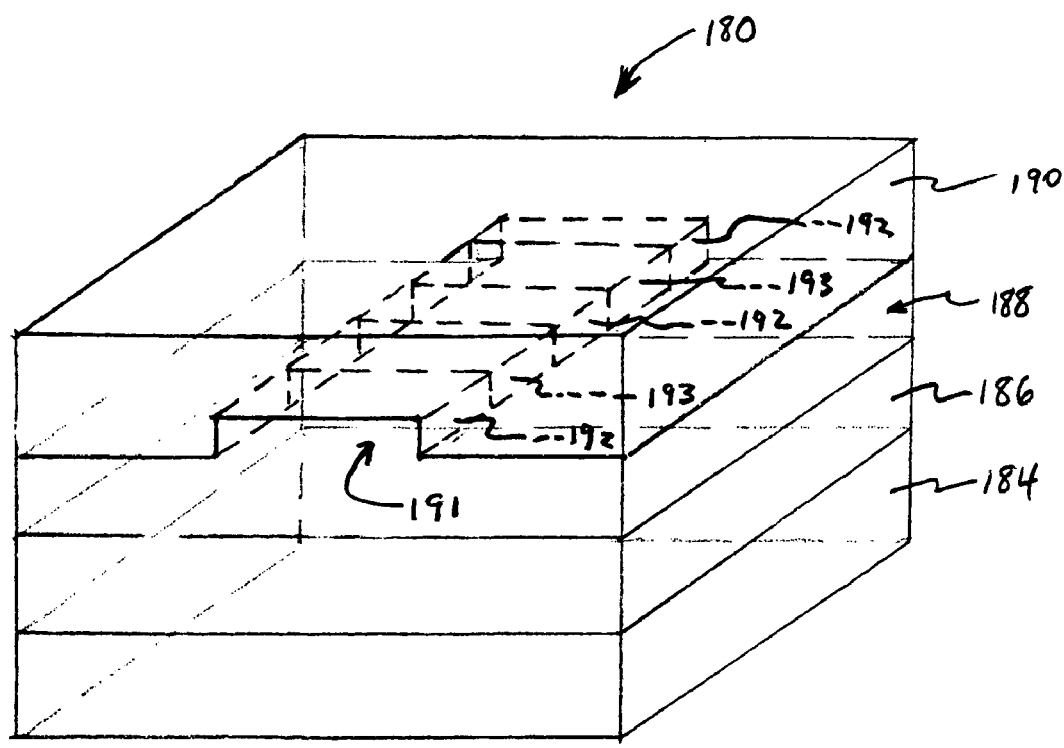
FIG. 15 is a diagrammatic isometric view of a ridge-type channel-type lightguide in which segmentation is achieved by locally desensitizing a sensitive layer.
Figure 16:
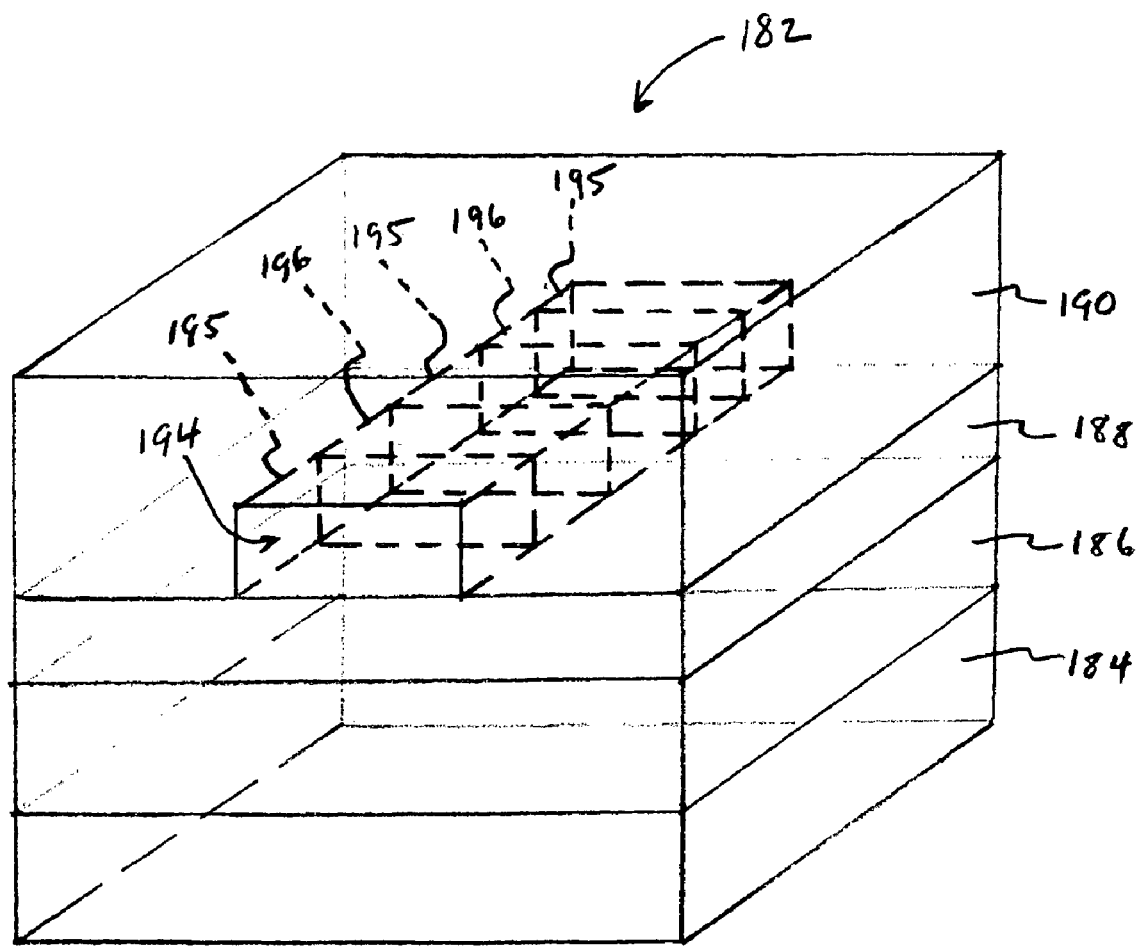
FIG. 16 is a diagrammatic isometric view of a strip-loaded channel lightguide, in which both the channel and the segmentation have been defined by locally desensitizing a sensitive layer.

FIGS. 15 and 16 show two channel-type lightguides, a ridge-type channel lightguide 180 in FIG. 15 and a strip-loaded type channel lightguide 182 in FIG. 16. Each lightguide includes a carrier layer 184, a buffer layer 186, a core layer 188 and a cladding layer 190. The ridge of a ridge-type channel lightguide is formed by a geometric change, such as a local thickening 191 in the core layer 188 forming alternating segments 192, 193. In the strip-loaded type channel lightguide 182, a cladding shaped as a strip 194 of alternating segments 195, 196 is provided on top of the core layer 188. Both lightguides include the second inclusion or cladding layer 190.

Figure 17:
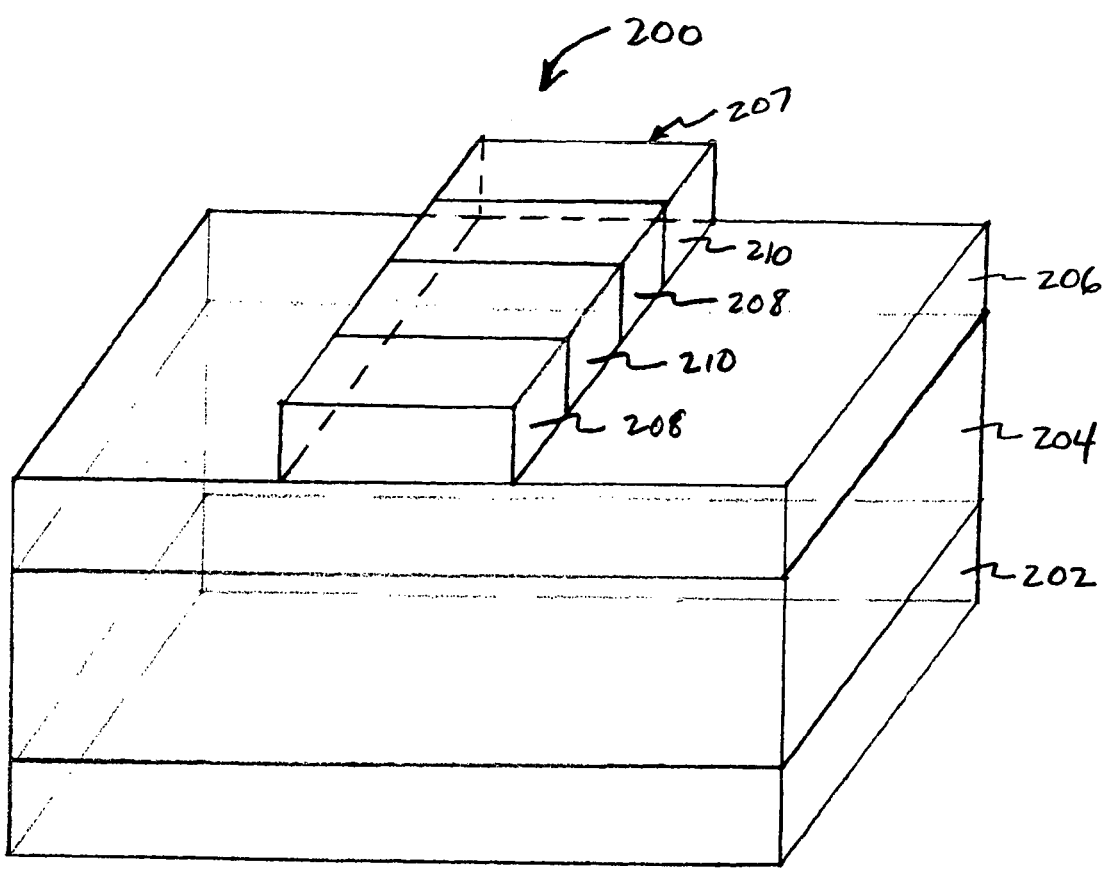
FIG. 17 is a diagrammatic isometric view of asegmented strip-loaded channel guide, of which segmentation has been achieved by locally desensitizing the sensitive strip material.

FIG. 17 illustrates a segmented strip-loaded type channel lightguide 200 which includes a carrier layer 202, a buffer layer 204, a core layer 206 but no second inclusion layer. The lightguide contains a strip 207 of alternating parameter sensitive segments 208 and desensitized segments 210, which together provide a light transmission channel.

Figure 18:
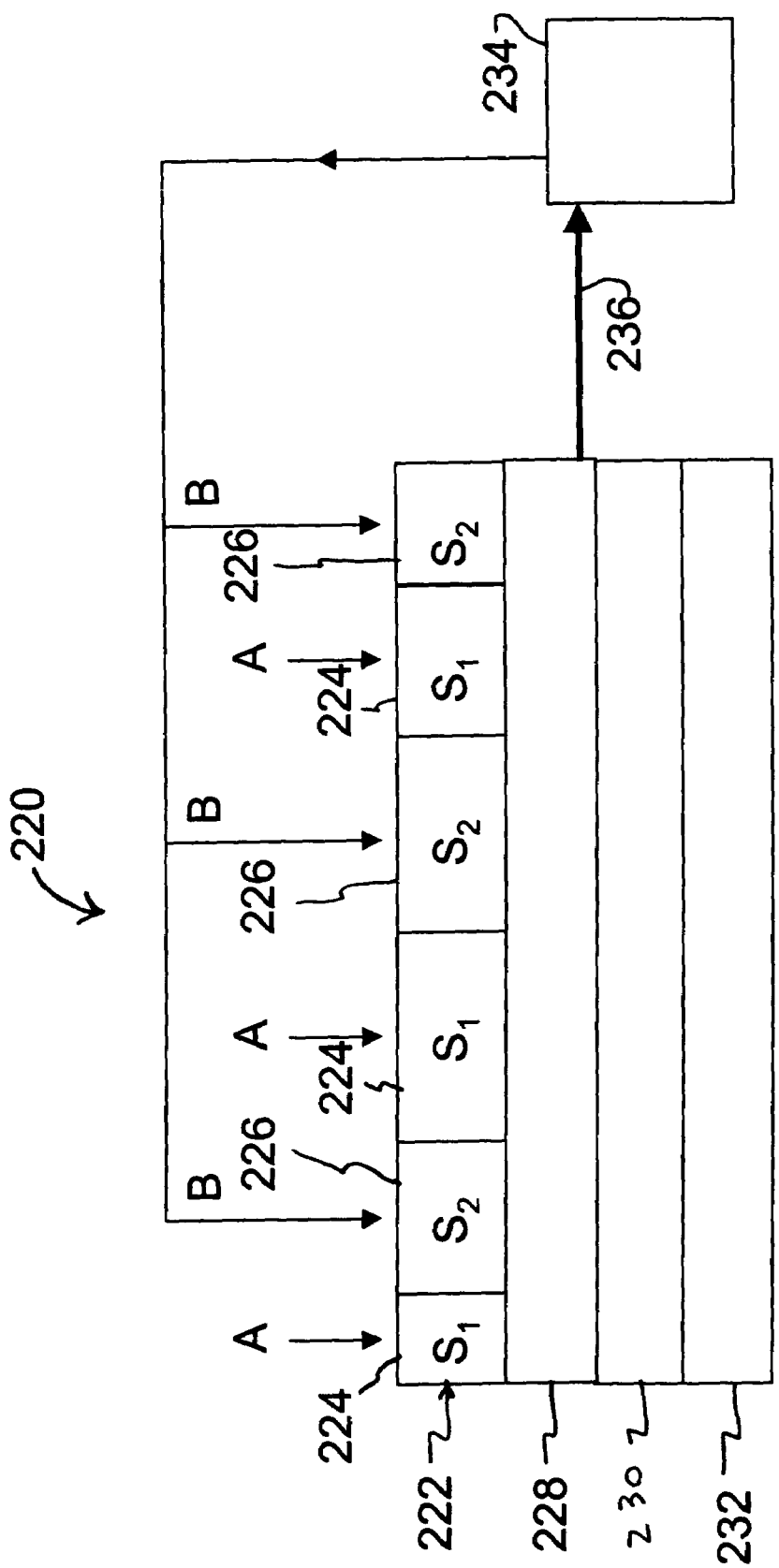
FIG. 18 is a diagrammatic longitudinal sectional elevation view of a lightguide with feedback capabilities.

Referring now to FIG. 18, there is illustrated a lightguide 220 and two types of non-periodic parameter sensitive segments in a cladding layer 222. For example, one type of segment $S_1$ 224 is formed of chemico-optical material and the other type of segment $S_2$ 226 is formed of electro-optical material. Beneath the cladding layer 222 are a core layer 228, a buffer layer 230 and a silicon wafer 232. The cross-sectioned dimensions of both types of segments are the same and the respective refractive indices are related in that they are identical for relevant values of each measurand.

At the working point, transmitted light intensity is at a maximum. When the refractive index of the segments 224 changes by virtue of the presence of parameter A, the refractive index of the segments 226 can be changed by altering parameter B, such as an electric field through a control system 234 where the control system is part of a feedback loop that detects light intensity 236 transmitted through the lightguide and seeks to return that intensity to its original maximum value after it is diminished in response to parameter A. This allows parameter A, a chemical concentration, for example, to be measured as a function of the electric field needed to equalize the refractive indices of the two types of segments 224, 226.

The above specification describes in detail the preferred embodiments of the present invention. Other examples, embodiments, modifications and variations will, under both the literal claim language and the doctrine of equivalents, come within the scope of the invention defined by the appended claims. Further, they will come within the literal language of the claims. Still other alternatives will also be equivalent as will many new technologies. There is no desire or intention here to limit in any way the application of the doctrine of equivalents nor to limit or restrict the scope of the invention.

What is claimed is:

1. A method for varying the output power of an integrated optical lightguide device comprising the steps of:
providing a lightguide device;
locating a light source at an entrance of said lightguide device;
locating a light detector at an exit of said lightguide device;
transmitting light through said lightguide device in a direction of light propagation;
forming in a non-periodic or arbitrary length distribution different types of segments in said lightguide device, each type of segment having a different refractive index profile in a plane perpendicular to said direction of light propagation wherein the refractive index profile of at least one type of segment is sensitive to an external physical parameter or chemical compound activating said at least one type of segment;
using refractive index profile dependent attenuation of guided modes passing transitions between two different segments; and
providing a lightguide channel including a light transmitting layer of an electro-optical material, wherein, in order to obtain light modulation, activating segments of one type by means of an electrical potential difference between two electrodes patterned in an electrically conductive intermediate layer on either side of said lightguide channel.

2. A method for varying the output power of an integrated optical lightguide device comprising the steps of:
providing a lightguide device;
locating a light source at an entrance of said lightguide device;
locating a light detector at an exit of said lightguide device;
transmitting light through said lightguide device in a direction of light propagation;
forming in a non-periodic or arbitrary length distribution different types of segments in said lightguide device, each type of segment having a different refractive index profile in a plane perpendicular to said direction of light propagation wherein the refractive index profile of at least one type of segment is sensitive to an external physical parameter or chemical compound activating said at least one type of segment;
using refractive index profile dependent attenuation of guided modes passing transitions between two different segments; and
wherein use is made of light transmitting layer comprising a thermo-optical material and wherein activating segments of one type by means of an electrical current driven through an electrical conducting intermediate layer introducing a segment pattern corresponding with a predetermined pattern of segments activated by an external physical parameter or chemical compound.

3. A method for determining a physical or chemical parameter using an integrated optical lightguide device comprising the steps of:
providing a lightguide device;
locating a light source at an entrance of said lightguide device;
locating a light detector at an exit of said lightguide device;
transmitting light through said lightguide device in a direction of light propagation;
forming in a non-periodic or arbitrary length distribution several types of segments in said lightguide device, each type of segment having a different refractive index profile in a plane perpendicular to the direction of light propagation wherein the refractive index profile of at least one type of segment is sensitive to an external physical parameter or chemical compound activating said at least one type of segment;
using refractive index profile dependent attenuation of guided modes passing transitions between two different segments;
measuring an amount of light entering said lightguide device in the form of one or more guided modes;
measuring an amount of light leaving the lightguide device in the form of guided modes; and
determining a ratio between the amount of light entering said lightguide device and the amount of light leaving said lightguide device, wherein said lightguide device comprises two types of segments $S_1$ and $S_2$, wherein $S_1$ is activated by a quantity A and $S_2$ is activated by a quantity B different from A and wherein $S_1$ and $S_2$ are incorporated in a feedback circuit and wherein, based on a constant transmission by the lightguide device, a relationship of a refractive index profile of $S_2$ to that of a refractive index profile of $S_1$ is maintained by applying a suitable value B, from which the quantity A is deduced.

4. An optical lightguide device comprising:
a light source at an entrance side;
a light detector at an exit side;
an integrated optical lightguide device wherein a light transmitting layer comprises an electro optical material in which an electric potential difference is applied between a first electrically conductive layer deposited on a first side of said electro optical material and a second electrically conducting layer deposited on an opposite side of said electro optical material wherein an electrode pattern is formed; and
a series of two types of segments spaced in a non-periodic manner along a direction of light propagation, which non-periodic manner is determined by the electrode pattern wherein one type of segment shows a refractive index distribution in a plane perpendicular to the direction of light propagation which is a function of said applied electrical potential difference.

5. An integrated optical device comprising:
a first structure extending along a light path, said first structure having light transmitting properties at a first refractive index distribution in a plane perpendicular to the direction of light propagation;
a second structure extending along the light path and in optical communication with said first structure, said second structure having light transmitting properties at a second refractive index distribution in a plane perpendicular to the direction of light propagation, said second refractive index distribution being different from said first refractive index distribution; and
a third structure extending along the light path and in optical communication with said second structure, said third structure having at least a plurality of first and second segments, each segment of said plurality of first segments having a refractive index distribution in a plane perpendicular to the direction of light propagation which is different from a refractive index distribution in a plane perpendicular to the direction of light propagation of each of said segments of said plurality of second segments, and each segment of said plurality of first segments being generally of unequal length compared to other segments of said plurality of first segments in the direction of said light path wherein a change in the amount of light transmitted by said integrated optical device is a function of a parameter being sensed.

6. The device of claim 5 wherein:
the lengths of said segments of said plurality of first segments are formed arbitrarily.

7. The device claim 5 wherein:
said segments of said plurality of first segments are unevenly distributed.

8. The device of claim 5 wherein:
said segments of said plurality of first segments have depths which are generally unequal.

9. The device of claim 5 wherein:
said change in the amount of light is generally independent of wavelength.

10. The device of claim 5 wherein:
said segments of said plurality of first segments have various geometric shapes.

11. An integrated optical lightguide comprising:
a first light transmitting structure;
a second light transmitting structure, said second light transmitting structure consisting only of a strip of a material sensitive to a physical parameter or a concentration of a chemical compound, said strip having been formed into alternating non-periodic first and second segments by desensitizing said second segments.

12. An integrated optical lightguide comprising:
a first light transmitting structure;
a second light transmitting structure having a ridge in optical communication with said first light transmitting structure, said ridge of said second light transmitting structure having a series of alternating non-periodic segments of sensitive material and desensitized material.

13. An integrated optical device comprising:
a first light transmitting structure;
a second light transmitting structure having segments of alternating active material and non-sensitive material, wherein initially both sensitive and non-sensitive material segments have different refractive index profiles and when a sensed parameter obtains a predetermined value the refractive index distribution of said segments of sensitive material has changed to such a value that it generally matches the refractive index distribution of said segments of non-sensitive material.

14. An integrated optical device comprising:
a first light transmitting structure; and
a second light transmitting structure having alternating segments $S_1$ and $S_2$ wherein changes to the refractive index distribution of said segments $S_1$ are caused by a change in one parameter from a first group of parameters consisting of a magnetic field, temperature, a force and a chemical concentration, and changes to the refractive index distribution of said segments $S_2$ is caused by a change in one parameter from a second group of parameters consisting of temperature, a magnetic field, an electric field and a force provided that the parameter of said second group is not the parameter of said first group that caused the change in refractive index distribution of said segments $S_1$.

15. A method for measuring an external physical parameter or a concentration of a chemical compound by measuring both input and output power of an integrated optical lightguide comprising the steps of:
providing a lightguide;
transmitting light through said lightguide in a direction of light propagation; and
forming in a non-periodic distribution in the direction of the light propagation different types of segments, each type of segment having a different refractive index profile in a plane perpendicular to said direction of light propagation, with one type of segment being sensitive to said external physical parameter or said concentration of a chemical compound.

16. A method for measuring an external physical parameter or a concentration of a chemical compound by measuring both input and output power of an integrated optical lightguide comprising the steps of:
providing a lightguide;
transmitting light through said lightguide in a direction of light propagation;
forming in the direction of light propagation a ridge-type light channel of a material sensitive to said physical parameter or to said concentration of a chemical compound; and
desensitizing a series of spaced apart segments of said material to form a ridge of alternating non-periodic sensitive and desensitized segments.

17. A method for measuring an external physical parameter or a concentration of a chemical compound by measuring both input and output power of an integrated optical lightguide comprising the steps of:
providing a lightguide;
transmitting light through said lightguide in a direction of light propagation;
forming in the direction of light propagation a cladding layer of material sensitive to said physical parameter or to said concentration of a chemical compound; and
desensitizing a series of spaced apart segments of said cladding layer material to form a series of alternating non-periodic sensitive and desensitized segments.

18. A method for measuring an external physical parameter or a concentration of a chemical compound by measuring both input and output power of an integrated optical lightguide comprising the steps of:
providing a lightguide;
transmitting light through said lightguide in a direction of light propagation;
forming in the direction of light propagation a strip loaded light channel, said strip formed of material sensitive to said physical parameter or to said concentration of a chemical compound; and
desensitizing a series of spaced apart segments of said strip to form a series of non-periodic alternating sensitive and desensitized segments.

19. A method for measuring an external physical parameter or a concentration of a chemical compound by measuring both input and output power of an integrated optical lightguide comprising the steps of:
providing a lightguide;
transmitting light through said lightguide in a direction of light propagation;
forming in a direction of light propagation two types of segments $S_1$ and $S_2$ wherein $S_1$ is sensitive to a quantity A and $S_2$ is activated by a quantity B different from A and wherein $S_1$ and $S_2$ are part of a feedback circuit; and activating $S_2$ in response to changes in the refractive index profile of $S_1$, which changes are a function of the presence of A, to maintain a constant transmission by the lightguide.

20. A method varying the output power of an integrated optical lightguide comprising the steps of:
  providing a lightguide;
  transmitting light through said lightguide in a direction of light propagation;
  forming in the direction of light propagation a ridge-type light channel of a material sensitive to a physical parameter or to a concentration of a chemical compound; and
  desensitizing a series of spaced apart segments of said material to form a non-periodic ridge of alternating sensitive and de-sensitized segments.

21. A method varying the output power of an integrated optical lightguide comprising the steps of:
  providing a lightguide;
  transmitting light through said lightguide in a direction of light propagation;
  forming in the direction of light propagation a cladding layer of material sensitive to a physical parameter or to a concentration of a chemical compound; and
  desensitizing a series of spaced apart segments of said cladding layer material to form a series of alternating non-periodic sensitive and desensitized segments.

22. A method varying the output power of an integrated optical lightguide comprising the steps of:
  providing a lightguide;
  transmitting light through said lightguide in a direction of light propagation;
  forming in the direction of light propagation a strip loaded light channel, said channel formed of material sensitive to a physical parameter or to a concentration of a chemical compound; and
  desensitizing a series of spaced apart segments of said channel to form a series of alternating non-periodic sensitive and desensitized segments.

23. A method for measuring a physical parameter or a concentration of a chemical compound A using an integrated optical lightguide comprising the steps of:
  providing a lightguide;
  transmitting light through said lightguide in a direction of light propagation;
  forming in a direction of light propagation two types of segments $S_1$ and $S_2$ wherein $S_1$ is sensitive to a quantity A and $S_2$ is activated by a quantity B different from A and wherein $S_1$ and $S_2$ are part of a feedback circuit; and
  activating $S_2$ in response to changes in the refractive index profile of $S_1$, which changes are a function of the presence of A, to maintain a constant transmission by the lightguide.

24. An integrate optical lightguide comprising:
  a light transmitting layer of electro-optical material;
  a first electrically conductive layer to one side of said light transmitting layer; and
  a second electrically conductive layer to an opposite side of said light transmitting layer, said second electrically conductive layer having a pattern such that application of a voltage creates an alternating segmentation, the alternating segmentation having a non-periodic distribution whereby the value of an applied voltage determines the refractive index profile of selective segments.

\* \* \* \* \*